United States Patent [19]

Marler et al.

[11] Patent Number: 5,302,769
[45] Date of Patent: Apr. 12, 1994

[54] PROCESS FOR MAKING ALKYLATED POLYCYCLIC AROMATICS

[75] Inventors: David O. Marler, Deptford; Dominick N. Mazzone, Wenonah; L. Deane Rollmann, Moorestown, all of N.J.

[73] Assignee: Mobil Oil Corporation, Fairfax, Va.

[21] Appl. No.: 986,187

[22] Filed: Dec. 7, 1992

[51] Int. Cl.$^5$ .................. C07C 2/66; C07C 15/24; C07C 15/27

[52] U.S. Cl. .................. 585/455; 585/25; 585/26; 585/467

[58] Field of Search .................. 585/467, 455, 25, 26

[56] References Cited

U.S. PATENT DOCUMENTS

| | | | |
|---|---|---|---|
| 2,527,335 | 10/1950 | Richter et al. | 260/329 |
| 4,079,093 | 3/1978 | Winter, III | 585/465 |
| 4,181,597 | 1/1980 | Yan et al. | 208/46 |
| 4,225,737 | 9/1980 | Milkulicz et al. | 585/464 |
| 4,795,847 | 1/1989 | Weitkamp et al. | 585/467 |
| 4,876,408 | 10/1989 | Ratcliffe et al. | 585/467 |
| 4,954,663 | 9/1990 | Marler et al. | 568/791 |
| 4,962,256 | 10/1990 | Le et al. | 585/467 |
| 4,992,606 | 2/1991 | Kushnerick et al. | 585/467 |
| 5,001,295 | 3/1991 | Angevine et al. | 585/467 |
| 5,053,573 | 10/1993 | Jorgensen et al. | 585/475 |

FOREIGN PATENT DOCUMENTS

| | | | |
|---|---|---|---|
| 63-14737 | 1/1988 | Japan | 585/467 |
| 4-02473 | of 1992 | Japan | |

OTHER PUBLICATIONS

CA 117(1):7627c.
"Recent Advances in the Chemistry of Dibenzothiophenes", Ashby et al., *Advances in Heterocyclic Chemistry*, vol. 16, pp. 221-230 (1974).
D. Fraenkel et al., "Shape-Selective Alkylation of Naphthalene and Methylnaphthalene with Methanol over H-ZSM-5 Zeolite Catalysts", 101, J. Catal., pp. 273-283 (1986).

*Primary Examiner*—Anthony McFarlane
*Attorney, Agent, or Firm*—Alexander J. McKillop; Malcolm D. Keen; Jessica M. Sinnott

[57] ABSTRACT

A polycyclic aromatic is contacted with an alkyl-substituted single ring aromatic, such as toluene, o-, m- or p-xylene or mesitylene, over a catalyst comprising a zeolite, such as zeolite beta, USY or ZSM-5 to alkylate the polycyclic aromatic. The polycyclic aromatic can be a fused polynuclear aromatic, e.g. phenanthrene, or an assembly of two or more cyclic systems, e.g. biphenyl. The polycyclic aromatic can also include carbocyclic systems such as fluorene and naphthalene or heterocyclic systems such as benzothiophene and dibenzothiophene. The polycyclic aromatic can be derived from a cycle oil, coker gas oil, extract of lubricant solvent refining or crude distillate fraction. The transalkylating agent can be derived from a reformate, pyrolysis gasoline or coker naphtha.

22 Claims, No Drawings

PROCESS FOR MAKING ALKYLATED POLYCYCLIC AROMATICS

FIELD OF THE INVENTION

The invention is directed to a method for making alkylated polycyclic aromatics. Specifically, the invention is directed to contacting a polycyclic aromatic with a short chain alkyl-substituted aromatic over a crystalline metallosilicate alkylation/transalkylation catalyst to alkylate the polycyclic aromatic. The invention is also directed to converting $C_9+$ single-ring aromatics into their more valuable lower boiling analogs.

BACKGROUND OF THE INVENTION

Methyl and other lower alkyl-substituted polycyclic aromatic compounds are considered useful precursors for making lubricant additives and polymers for high temperature conditions. Methyl-substituted polycyclic aromatics have been prepared on a laboratory scale from expensive reagents such as butyl-lithium and dimethyl-sulfate. However, because these reagents can be considered hazardous and the costs of using them are high, this is not an acceptable large-scale synthesis route.

Large scale refinery production of alkyl-substituted aromatics by alkylating heavy aromatics-rich refinery streams has been considered as a means for upgrading low value refinery by-products such as fluid catalytically cracked (FCC) cycle oils, thermofor catalytically cracked (TCC) cycle oils, coker gas oils and aromatic extracts from lubricant manufacturing facilities which are typical relatively heavy aromatics-rich by-product streams.

Conversion of polycyclic aromatics with a lower alcohol, such as methanol over a catalyst containing a zeolite, such as ZSM-5, has been described. See, for example, D. Fraenkel et al "Shape-Selective Alkylation of Naphthalene and Methylnaphthalene with Methanol over H-ZSM-5 Zeolite Catalysts", 101 J. Catal. p. 273 (1986). However, this method tends to result in a high catalyst aging rate because it exposes the catalyst to water vapor at high temperatures which reduces the useful life of the catalyst. Different approaches along this line have been described in U.S. Pat. Nos. 4,992,606; 4,795,847; 2,527,335; 5,001,295; 4,954,663; 4,962,256; 4,181,597; and 5,053,573. For example, in U.S. Pat. No. 4,795,847, a process for the preparation of 2,6-dialkyl-naphthalenes is described in which naphthalene, or 2-alkyl-naphthalene is selectively alkylated with an alkylating agent such as methanol, dimethylether or methyl bromide.

Methyl-substituted polynuclear aromatics and thiophenes have been synthesized in multi-step procedures involving adorption/desorption, extraction, reaction and purification, as described in M. Radke, "Organic Geochemistry of Aromatic Hydrocarbons", *Advances in Petroleum Geochemistry*, Vol. 2, p. 141 (1987) and J. Ashby et al "Recent Advances in the Chemistry of Dibenzothiophenes" *Advances in Heterocyclic Chemistry*, Vol. 16, p. 181 (1974). However, these processes would not provide a practical large scale solution to the problem of converting cycle oils to more valuable refinery products.

U.S. Pat. No. 5,053,573 discloses a process for converting benzene to heavier aromatics by alkylating the benzenes of a reformate with alkyl polynuclear aromatics over an alkylation/transalkylation catalyst. This process successfully converts high benzene fractions to more acceptable alkylated benzenes useful as high octane gasoline. However, this process does not describe upgrading the polycyclic aromatics to alkylated polycyclic aromatics.

SUMMARY OF THE INVENTION

It is an object of this invention to make alkyl-substituted polycyclic aromatics, useful as lubricant additive precursors.

It is a further object of this invention to upgrade polyalkylated single ring aromatics to gasoline boiling range products.

It is a feature of this invention to simultaneously produce alkyl-substituted polycyclic aromatics while upgrading the polyalkylated single ring aromatics by reacting a polycyclic aromatic with a short-chain polyalkyl-substituted aromatic, more specifically a di-, tri- or tetra-methyl-substituted aromatic, over a catalyst containing a crystalline metallosilicate under conditions sufficient to effect alkylation of the polycyclic aromatic.

Accordingly, the invention is directed to a method of making an alkylated polycyclic aromatic comprising contacting a polycyclic aromatic with a short-chain alkyl-substituted single ring aromatic in the presence of an alkylation/transalkylation catalyst containing a crystalline metallosilicate under conditions sufficient to effect alkylation of the polycyclic aromatic.

DETAILED DESCRIPTION OF THE INVENTION

A polycyclic aromatic useful in this process can be derived from a feedstock which is substantially dealkylated and hydrogen deficient. The type of feedstock contemplated can contain one or more fused-ring polycyclic aromatic compounds and/or assemblies of two or more cyclic systems, either single ring cyclics and aromatics or fused systems. Fused systems are rings which are joined directly to each other by double or single bonds.

The polycyclic aromatic feedstock is usually obtained from catalytic cracking operations, e.g. FCC or TCC. Typically, these feedstocks have a hydrogen content of no greater than about 12.5 wt. % and API gravity no greater than 25 and an aromatic content no less than 50 wt. %.

A substantially dealkylated feedstock is a product which was formerly an alkyl aromatic which contained bulky relatively large alkyl group side chains affixed to the aromatic moiety. The dealkylated product is the aromatic moiety having no bulky side chain alkyl group. Representative examples of the aromatic moiety include phenanthrene, dibenzothiophene, fluoroanthene, fluorene, benzothiophene, acenaphthene, biphenyl or naphthalene.

Because of the mechanism of acid catalyzed cracking and similar reactions, it may be assumed that prior dealkylation will remove side chains of greater than 5 carbon atoms while leaving behind primarily methyl or ethyl groups on the aromatic moieties. Thus, for purposes of this invention the polycyclic aromatic can include substantially dealkylated aromatics which contain small alkyl groups, such as methyl and sometimes ethyl and the like, remaining as side chains, but with relatively few large alkyl groups, e.g. the $C_3$ to $C_9$ groups remaining.

The polycyclic aromatic can comprise a mixture of polycyclic compounds, dealkylated or substantially dealkylated, which would be found in a refinery by-product stream. Alternatively, it can be a relatively pure feed consisting essentially of one type of polycyclic aromatic compound.

Representative examples of suitable polycyclic aromatic refinery by-product derived feedstocks include light cycle oils and heavy cycle oils from catalytic cracking processes. Other examples of suitable feedstocks include the liquid product from a delayed or fluid bed coking process, such as a coker gas oil, an aromatics-rich fraction produced by lubricant refining, e.g. furfural extraction. Other sources of suitable feedstocks include a heavy crude fraction obtained by crude fractional distillation.

Specifically, the polycyclic aromatic contemplated contains at least 2 cyclic groups and up to at least 5 cyclic groups. More specifically, the polycyclic aromatic contains at least 3 cyclic groups. It can be a hydrocarbon containing up to 5 or more benzene rings in any arrangement including fixed benzene rings in linear arrangement. It can be almost entirely or predominantly carbocyclic and can include or be part of a heterocyclic system in which at least one of the cyclic elements of the molecule contains at least one heteroatom such as sulfur, nitrogen and/or oxygen.

The polycyclic aromatic is contacted with an aromatic transalkylating agent, more specifically, an alkyl-substituted single ring aromatic. The alkyl-substituted single ring aromatic can have one to four short chain alkyl substituents. Preferably, the short chain alkyl substituent contains from 1 to 2 carbon atoms, such as methyl and ethyl. Most preferably the short chain hydrocarbon is methyl, in which instance the single ring aromatic is considered a transmethylating agent. Representative examples of transalkylating agents include methylbenzene (toluene), ortho-, meta- or para-dimethylbenzene (e.g. o-, m- or p- xylene), trimethylbenzene (e.g. mesitylene or pseudocumene) and tetramethylbenzene (e.g. durene).

The source of single ring aromatic can be a reformate fraction or any other methyl substituted single ring aromatic-rich feed. Specific examples include a reformate from a swing bed or moving bed reformer. Although a most useful source of these single ring aromatics is a reformate fraction, other useful sources include pyrolysis gasoline, coker naphtha, methanol-to-gasoline, or other zeolite catalyst olefin or oxygenate conversion process wherein significant aromatics product is obtained. Another contemplated source is the heavy side product of various aromatics conversion processes (e.g. toluene disproportionation and xylene isomerization).

An important advantage to using the single ring aromatic as a transalkylating agent, instead of alkylating with an alcohol or alkylhalide, is the resulting conversion of the single ring aromatic to a gasoline boiling range product, without the production of benzene. That is, we have found that polyalkylated alkylating agents are not entirely dealkylated by the reaction.

Another important advantage of using the transalkylating agent over an alcohol, such as methanol, or an alkylhalide is a reduction in catalyst aging rate since the catalyst is not exposed to the steam produced by reaction with alcohol or the acid produced by reaction with alkylhalide.

The catalyst used in the process of this invention is an acidic, or acid-acting, catalyst. The classes of suitable catalysts include crystalline metallosilicates, such as zeolites. Other acidic oxides may also be suitable. Although clays may be suitable they are not preferred. These solid catalysts are useful in fluid and fixed bed catalysis, and, being heterogeneous to the reactants, are readily separable therefrom.

The choice of catalyst most useful for this process will depend upon the feedstock and, in some cases, to the product desired. For example, with the larger polycyclic aromatic which contains over about 2 aromatic rings, the pore size of the catalyst must be sufficiently large since the pore size constraints of the zeolite can hinder admittance of these bulky molecules. Thus, the preferred catalysts for this invention are the large pore zeolitic behaving catalytic materials. These zeolitic catalytic materials are exemplified by those which, in their aluminosilicate form would have a Constraint Index ranging from up to about 2, preferably from about 0.2 to 2 and more preferably, less than 1. Reference is here made to U.S. Pat. No. 4,784,745 for a definition of Constraint Index and a description of how this value is measured. The preferred catalytic materials having the appropriate functionality include mordenite, zeolite beta, faujasites such as zeolite Y, Ultra Stable Y (USY), ZSM-4 and ZSM-20.

Other zeolitic catalytic materials may find utility in this process particularly with feeds which are predominantly composed of polycyclic systems having two rings, such as naphthalene, alkyl-substituted naphthalenes such as mono- and di-methylnaphthalene, biphenyl and benzothiophene. A particular class of catalytic materials having the appropriate functionality include those having the topology of ZSM-5, ZSM-11, ZSM-12, ZSM-22, ZSM-23, ZSM-35, ZSM-48, ZSM-50 and MCM-22.

The catalytic materials described are exemplary of the topology and pore structure of suitable acid-acting refractory solids; useful catalysts are not confined to the aluminosilicates, and other refractory solid materials which have the desired acid activity, pore structure and topology may also be used. The crystalline zeolites have a porous, robust framework. The framework consists primarily of silicon tetrahedrally coordinated and interconnected with oxygen bridges. Other framework components, for example, may include Group IIIB elements of the Periodic Table, e.g. aluminum, boron and gallium. Other elements such as phosphorus and iron may be included as framework components. Aluminum phosphates and silico-aluminum phosphates are specifically contemplated. The zeolite designations referred to above, for example, define the topology only and do not restrict the compositions of the zeolitic-behaving catalytic components.

The catalyst should have sufficient acid activity and selectivity to promote the alkylation/transalkylation, more specifically methylation/transmethylation, reactions at reasonable temperatures and catalyst space velocities. Transalkylation is specifically defined herein as the transfer of one or more lower alkyl groups, such as methyl, from the substituted single ring aromatic to the polycyclic aromatic.

The active component of the catalyst e.g. the zeolite will usually be used in combination with a binder or substrate because the particle sizes of the pure zeolitic behaving materials are often too small and lead to an excessive pressure drop in a catalyst bed. This binder or substrate, which is preferably used in this service, is suitably any refractory binder material. Examples of these materials are well known and typically include silica, silica-alumina, silica-zirconia, silica-titania, alumina, titania or zirconia.

The particle size and the nature of the conversion catalyst will usually be determined by the type of conversion process which is being carried out, such as: a down-flow, liquid phase, fixed bed process; an up-flow, fixed bed, liquid phase process; an ebullating, fixed fluidized bed liquid or gas phase process; or a liquid or gas phase, transport, fluidized bed process, as noted above, with the fixed-bed type of operation preferred.

The lower limits on catalyst activity and on reactive conditions are sufficient to convert at least 10% and preferably 25% of the polyclic aromatics in the feed. By conversion of the polycyclic aromatics, we mean, most specifically, the addition of molecular weight (e.g. methyl) side chains. The total number of moles of polycyclic aromatic in the product will normally be about the same as the total moles of polycyclic aromatic in the feed to the reactor. The degree of methylation ranges from about 10 to 95%, preferably from at least about 50%.

The product will have an overall boiling range conversion, e.g. alkyl group transfer from molecules in the gasoline boiling range, to those boiling at and above the range of distillates, the latter being typically within the range of about 400° F. to about 752° F. (204° C. to 400° C.).

With most catalysts, the following reaction conditions can be used. Temperatures may range from about 370° C. to 600° C. (700° F. to 1100° F.), more specifically from about 400° C. to about 470° C. (750° F. to 880° F.). Although fluidized, fixed or moving bed reactors can be used, the relative ratios of feed to catalyst, as applied to fixed beds will be provided. Weight hourly space velocities (WHSV) of from about 0.5 to 15, more specifically from about 1 to about 10 will usually give good results. Pressures may range from atmospheric, or even subatmospheric to relatively high pressures and usually will range from about 1 to about 1000 psig. Oil partial pressures will normally range from about 100 psia to about 500 psia. Hydrogen is not essential, but the process may benefit from its presence, particularly in extending catalyst life. When hydrogen is added it typically ranges from about 0.5:1.0, to 5.0:1.0, expressed in terms of hydrogen to hydrocarbon mole ratio. The mole ratio of polycyclic aromatic to single ring aromatic falls within the range of about 1:10 to 10:1, more specifically from about 1:5 to 5:1.

EXAMPLES

The following examples demonstrate the effectiveness of the process of this invention in alkylating polycyclic aromatics with alkyl-substituted single ring aromatics. Unless otherwise noted, all experiments were conducted in a downflow fixed bed tubular reactor, at 500 psig hydrogen, 820° to 830° F. inlet temperature, weight hourly space velocity (WHSV) ranging from 4 to 6, and a hydrogen to hydrocarbon mole ration of about 2. The mole ratio of polycyclic aromatic to single ring aromatic was about 1:9. Hydrogen alone was the overnight and overweekend feed. Isomer distribution among the product alkylated/polyalkylated polycyclic aromatics was determined by gas chromatography based on the description on M. L. Lee et al, *Anal. Chem.*, Vol. 51 p. 768 (1979) and on the boiling points of known compounds.

Each catalyst used was prepared from an ammonium-ion exchanged and calcined zeolite bound with alumina (65% zeolite/35% alumina). The catalysts were sized to 24/60 mesh for testing.

Example 1

This example demonstrates methyl group transfer from di- and tri-methyl benzenes (e.g. m-xylene and mesitylene) to polynuclear aromatics (e.g. dibenzothiophene, phenanthrene, and naphthalene) over a USY zeolite thermally treated to a silica-to-alumina mole ratio of about 220.

TABLE 1

| Transmethylation of Polycyclic Aromatics over USY | | | | | |
|---|---|---|---|---|---|
| | Run | | | | |
| | 1 | 2 | 3 | 4 | 5 |
| Feed | MX/DBT | MX/DBT | MX/Phen | MX/Naph | TMB/DBT |
| WHSV | 5.2 | 5.4 | 5.7 | 5.1 | 5.5 |
| Days on Stream | 2 | 7 | 6 | 8 | 3 |
| Conversion, wt. % | | | | | |
| Alkyl. Agent | 19 | 13 | 9 | 13 | 46 |
| Polycyclic | 64 | 53 | 40 | 44 | 98 |
| Polycyclic product, mole % | | | | | |
| Parent polycyclic | 40 | 51 | 68 | 61 | 2 |
| Methyl deriv. polycyclic | 60 | 49 | 32 | 39 | 98 |
| $H_2S$, wt. % | 0.09 | 0.06 | 0.00 | 0.00 | 0.12 |

MX = Meta-xylene
DBT = dibenzothiophene
TMB = trimethylbenzene
Phen = phenanthrene
Naph = naphthalene From the results reported in Table 1, it is apparent that over a synthetic faujasite zeolite, there is effective alkylation of the polycyclic aromatics. The relative absence of $H_2S$ in the dibenzothiophene product stream (runs 1, 2 and 5) and the good agreement between the weight percent conversion of polycyclic aromatics to higher molecular weight polycyclic aromatics and mole % distribution between the parent polycyclic aromatic and the methyl derivative indicates an absence of major side reactions.

Example 2

This example demonstrates methyl group transfer from di-methyl benzenes (e.g. m-xylene) to polynuclear aromatics (e.g. dibenzothiophene, phenanthrene, and naphthalene) over a zeolite beta catalyst having a silica-to-alumina mole ratio of about 50.

TABLE 2

| Transmethylation of Polycyclic Aromatics over Zeolite Beta | | | | |
|---|---|---|---|---|
| | Run | | | |
| | 1 | 2 | 3 | 4 |
| Feed | MX/DBT | MX/DBT | MX/Phen | MX/Naph |
| WHSV | 5.1 | 5.1 | 5.3 | 4.9 |
| Days on Stream | 2 | 7 | 6 | 8 |
| Conversion, wt. % | | | | |
| Alkyl. Agent | 29 | 22 | 12 | 13 |
| Polycyclic | 71 | 59 | 36 | 35 |
| Polycyclic product, mole % | | | | |
| Parent Polycyclic | 33 | 44 | 78 | 71 |
| Methyl deriv. | 67 | 56 | 22 | 29 |

TABLE 2-continued

Transmethylation of Polycyclic Aromatics over Zeolite Beta

| | Run | | | |
|---|---|---|---|---|
| | 1 | 2 | 3 | 4 |
| Polycyclic H$_2$S, wt. % | 0.23 | 0.13 | 0.00 | 0.00 |

MX = Meta-xylene
DBT = dibenzothiophene
Phen = phenanthrene
Naph = naphthalene

From the results reported in Table 2, it is apparent that effective alkylation of the polycyclic aromatics with di-methyl single ring aromatics occurs over zeolite beta quite effectively. The relative absence of H$_2$S in the dibenzothiophene product stream (runs 1 and 2) and the generally good agreement between the weight percent conversion of polycyclic aromatics to higher molecular weight polycyclic aromatics and mole % distribution between the parent polycyclic aromatic and the methyl derivative indicates an absence of major side reactions.

Comparing the results of this Example with Example 1, a difference in the relative reactivity of dibenzothiophene and phenanthrene is noted. The zeolite beta catalyst is more selective for dibenzothiophene (as compared with phenanthrene) conversion while the USY is more selective for phenanthrene conversion.

Example 3

This example demonstrates methyl group transfer from mono-methyl benzenes (e.g. toluene) and di-methyl benzenes (e.g. m-xylene) to polynuclear aromatics (e.g. naphthalene, dibenzothiophene, and benzothiophene) over a ZSM-5 catalyst (silica-to-alumina mole ratio of 70). Toluene, with hydrogen flow, was the overnight and overweekend feed.

TABLE 3

Transmethylation of Polycyclic Aromatics over ZSM-5

| | Run | | | | |
|---|---|---|---|---|---|
| | 1 | 2 | 3 | 4 | 5 |
| Feed | T/Naph | MX/Naph | MX/BT | MX/DBT | MX/DBT |
| WHSV | 3.8 | 4.0 | 4.2 | 4.3 | 2.1 |
| Days on Stream | 7 | 12 | 16 | 13 | 14 |
| Conversion, wt. % | | | | | |
| Alkyl. Agent | 27 | 35 | 28 | 35 | 46 |
| Polycyclic | 5 | 15 | 70 | ~5 | ~10 |
| Polycyclic product, mole % | | | | | |
| Parent | 96 | 85 | 39 | 98 | 96 |

TABLE 3-continued

Transmethylation of Polycyclic Aromatics over ZSM-5

| | Run | | | | |
|---|---|---|---|---|---|
| | 1 | 2 | 3 | 4 | 5 |
| Methyl deriv. | 4 | 15 | 61 | 2 | 4 |
| H$_2$S, wt. % | 0.00 | 0.00 | 0.00 | 0.00 | 0.05 |

T = toluene
Naph = naphthalene
MX = Meta-xylene
DBT = dibenzothiophene
BP = benzothiophene From the results reported in Table 3, it is apparent that conversion of three-ring polycyclics (e.g. dibenzothiophene, Runs 4 and 5) was lower over ZSM-5 as opposed to conversion with the same reactants over USY and zeolite beta (compare Run 2 of Example 1 and Run 2 of Example 2 with Runs 4 and 5 of this example). This supports the view that the three ring polycyclics are generally excluded from the internal pore structure of the medium pore zeolite ZSM-5 and are converted instead on the catalytic sites which reside on the exterior of the crystal structure.

By contrast, conversion of two-ring polycyclics (e.g. naphthalene and benzothiophene, Runs 1, 2 and 3), over ZSM-5, was significant. Conversion of naphthalene over ZSM-5 was comparable to conversions achieved over zeolite beta and USY.

It is important to note that shape selectivity, e.g. preferential formation of 2,6-dimethylnaphthalene, was observed in the product obtained over ZSM-5.

Run 1, in which toluene was used as the alkylating agent achieved some small degree of methyl transfer, although it is clear that the di-methyl aromatic (meta-xylene, Run 2) was much more active.

Example 4

This example demonstrates the effectiveness of the process of this invention in alkylating a broad range of polycyclic aromatics with di- and tri- alkyl-substituted single ring aromatics. In the following Tables 4 and 5, the results of methyl group transfer from m-xylene and mesitylene to a broad range of polynuclear aromatics (e.g. dibenzothiophene, phenanthrene, methylnaphthalene, fluorene, acenaphthene and biphenyl) are reported. The experiment was conducted in a downflow fixed bed tubular reactor, at 500 psig hydrogen, 820 to 830 .F inlet temperature, weight hourly space velocity (WHSV) ranging from 5 to 6, and a hydrogen to hydrocarbon ratio of 2.5. A 1:9 mole ratio of polycyclic : single ring aromatic was used. The catalyst used was the same USY, as in Example 1.

TABLE 4

Transmethylation of Polycyclic Aromatic Over USY with Trimethybenzene

| | Run | | | | | | |
|---|---|---|---|---|---|---|---|
| | 1 | 2 | 3 | 4 | 5 | 6 | 7 |
| Polycyclic feed | DBT | DBT | DBT | DBT | DBT | DBT | Phen |
| Alkylating Agent | TMB | TMB | TMB | TMB | TMB | TMB | TMB |
| Polycyclic Conversion (mol. %) | 88 | 81 | 94 | 99 | 96 | 93 | 66 |
| Polycyclic Product Distribution (wt. %) | | | | | | | |
| Unsubstituted | 10 | 17 | 5 | 1 | 3 | 6 | 32 |
| Methylsubstituted | 32 | 39 | 24 | 10 | 18 | 26 | 45 |
| Dimethyl substituted | 36 | 32 | 38 | 29 | 37 | 38 | 19 |
| Tri(+)methylsubstituted | 21 | 12 | 33 | 60 | 42 | 29 | 4 |
| Reaction Conditions | | | | | | | |
| Inlet Temp. (°F.) | 829 | 829 | 829 | 820 | 820 | 829 | 829 |
| WHSV | 5.87 | 5.67 | 5.67 | 5.48 | 5.53 | 5.79 | 5.63 |

TABLE 4-continued
Transmethylation of Polycyclic Aromatic Over USY with Trimethybenzene

| | | | | | | | |
|---|---|---|---|---|---|---|---|
| H$_2$/HC ratio | 2.43 | 2.53 | 2.51 | 2.48 | 2.48 | 2.49 | 2.5 |
| Liquid balance, % | 97 | 98 | 98 | 102 | 101 | 98 | 99 |
| Mole balance, % | 88 | 88 | 95 | 85 | 86 | 93 | 68 |

| | Run | | | | | | |
|---|---|---|---|---|---|---|---|
| | 8 | 9 | 10 | 11 | 12 | 13 | 14 |
| Polycyclic feed | Phen | BT | BT | Fluo | Ace | BiP | 2MN |
| Alkylating Agent | TMB | TMB | TMB | TMB | TMB | TMB | TMB |
| Polycyclic Conversion (mol. %) | 58 | 73 | 35 | 64 | 57 | 60 | 39 |
| Polycyclic Product Distribution (wt. %) | | | | | | | |
| Unsubstituted | 40 | 24 | 62 | 34 | 40 | 36 | — |
| Methylsubstituted | 43 | 38 | 30 | 42 | 40 | 29 | 59 |
| Dimethyl substituted | 16 | 27 | 7 | 19 | 17 | 10 | 38 |
| Tri(+)methylsubstituted | 2 | 11 | 0 | 5 | 3 | 24 | 3 |
| Reaction Conditions | | | | | | | |
| Inlet Temp. (°F.) | 834 | 819 | 819 | 819 | 819 | 817 | 819 |
| WHSV | 5.67 | 5.69 | 5.69 | 5.66 | 5.62 | 5.43 | 5.22 |
| H$_2$/HC ratio | 2.50 | 2.40 | 2.40 | 2.47 | 2.47 | 2.54 | 2.59 |
| Liquid balance, % | 98 | — | 99 | 99 | 99 | 99 | 99 |
| Mole balance, % | 101 | 79 | 89 | 100 | 88 | 100 | 88 |

TMB = trimethylbenzene
DBT = dibenzothiophene
Phen = phenanthrene
BT = benzothiophene
Fluo = fluorene
Ace = acenaphthene
BiP = biphenyl
2MN = dimethylnaphthalene

TABLE 5
Transmethylation of Polycyclic Aromatic Over USY With Metaxylene

| | Run | | | |
|---|---|---|---|---|
| | 1 | 2 | 3 | 5–7 |
| Polycyclic Feed | DBT | BiP | Fluo | Phen |
| Alkylating Agent | MX | MX | MX | MX |
| Polycyclic conversion (mole %) | 61 | 40 | 46 | 34 |
| Polycyclic Product Distribution (wt. %) | | | | |
| Unsubstituted | 39 | 58 | 54 | 66 |
| Methylsubstituted | 46 | 22 | 35 | 29 |
| Dimethylsubstituted | 14 | 9 | 10 | 3 |
| Tri(+)methylsubstituted | 2 | 11 | 1 | 2 |
| Reaction Conditions | | | | |
| Inlet temp. (°F.) | 829 | 829 | 829 | 829 |
| WHSV | 5.56 | 5.51 | 5.66 | 5.74 |
| H$_2$/HC ratio | 2.25 | 2.94 | 2.20 | 2.1 |
| Liquid balance (%) | 99 | 100 | 100 | — |
| Mole balance % | 79 | 93 | 82 | 79 |

MX = metaxylene
DBT = dibenzothiaphene
BiP = biphenyl
Fluo = fluorene
Phen = phenanthrene

What is claimed is:

1. A process of making a methylated polycyclic aromatic comprising contacting a polycyclic aromatic which contains at least three cyclic groups with a methyl-substituted single ring aromatic in the presence of a transmethylation catalyst comprising a zeolite having the structure of a faujasite under conditions sufficient to effect methylation of the polycyclic aromatic.

2. The process of claim 1 in which the polycyclic aromatic which contains at least three cyclic groups is selected from the group consisting of dibenzothiophene, phenanthrene, fluorene and acenaphthene.

3. The process of claim 2 in which the methyl-substituted single ring aromatic is selected from the group consisting of meta-xylene and tri-methylbenzene.

4. The process of claim 2 in which the source of the polycyclic aromatic is a light cycle oil, heavy cycle oil, coker gas oil, ar aromatics-rich solvent extract of lubricant refining or a heavy crude fraction obtained from fractional distillation.

5. The process of claim 1 in which the polycyclic aromatic comprises a fused polycyclic aromatic.

6. The process of claim 1 in which the methyl-substituted single ring aromatic is a dimethylbenzene or a trimethylbenzene.

7. The process of claim 6 in which the trimethylbenzene is mesitylene or pseudocumene and the dimethylbenzene is meta-xylene.

8. The process of claim 1 in which the source of the methyl-substituted single ring aromatic is a reformate fraction, pyrolysis gasoline or coker naphtha.

9. The process of claim 1 in which the zeolite having the structure of a faujasite is zeolite Y or ultra stable Y.

10. A process of making a methylated polycyclic aromatic comprising contacting dibenzothiophene with a methyl-substituted single ring aromatic in the presence of a transmethylation catalyst comprising a zeolitic material having a Constraint Index of less than about 1 under conditions sufficient to effect methylate of the polycyclic aromatic.

11. The process of claim 10 in which the catalyst comprises zeolite beta or a faujasite.

12. The process of claim 11 in which the faujasite is zeolite Y or ultra stable Y.

13. A process of making a methylated polycyclic aromatic comprising contacting a polycyclic aromatic selected from the group consisting of biphenyl, benzothiophene, dibenzothiophene, phenanthrene, fluorene and acenaphthene with a methyl-substituted single ring aromatic in the presence of a transmethylation catalyst comprising a zeolite having the structure of a faujasite under conditions sufficient to effect methylation of the polycylic aromatic.

14. The process of claim 13 in which the methyl-substituted single ring aromatic is selected from the group consisting of dimethylbenzene and trimethylbenzene.

15. The process of claim 13 in which the methyl-substituted single ring aromatic is meta-xylene.

16. The process of claim 14 in which the trimethylbenzene is mesitylene or pseudocumene.

17. The process of claim 13 in which the zeolite having the structure of a faujasite is zeolite Y or ultra stable Y.

18. The process of claim 13 in which the source of the polycyclic aromatic is a light cycle oil, heavy cycle oil, coker gas oil or an aromatics-rich solvent extract of lubricant refining.

19. A process of making a methylated polycyclic aromatic comprising contacting a polycyclic aromatic selected from the group consisting of benzothiophene with a methyl-substituted single ring aromatic in the presence of a transmethylation catalyst comprising a zeolitic behaving material selected from the group consisting of a medium pore size zeolite under conditions sufficient to effect methylation of the polycyclic aromatic.

20. The process of claim 19 in which the medium pore zeolite is a zeolite having the topology of ZSM-5.

21. The process of claim 19 in which the methyl-substituted single ring aromatic is a xylene.

22. The process of claim 21 in which the xylene is meta-xylene.

* * * * *